(12) United States Patent  
McKay

(10) Patent No.: US 8,267,895 B2  
(45) Date of Patent: Sep. 18, 2012

(54) NEEDLE GUIDE SYSTEM

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 355 days.

(21) Appl. No.: 12/693,853

(22) Filed: Jan. 26, 2010

(65) Prior Publication Data

US 2011/0184350 A1    Jul. 28, 2011

(51) Int. Cl.  
*A61M 5/178*    (2006.01)

(52) U.S. Cl. .................................. 604/164.01

(58) Field of Classification Search ............. 604/117, 604/110, 111, 192, 198, 272, 164.01  
See application file for complete search history.

(56) References Cited

U.S. PATENT DOCUMENTS

| | | | |
|---|---|---|---|
| 5,312,351 A * | 5/1994 | Gerrone | 604/117 |
| 6,391,005 B1 * | 5/2002 | Lum et al. | 604/117 |
| 7,204,826 B2 | 4/2007 | Tremaglio et al. | |
| 2002/0022800 A1 | 2/2002 | O'Holloran et al. | |
| 2007/0129744 A1 | 6/2007 | Teichert et al. | |
| 2007/0149992 A1 | 6/2007 | Teng | |
| 2007/0179474 A1 * | 8/2007 | Cahill et al. | 604/533 |
| 2008/0077093 A1 | 3/2008 | Gratwohl et al. | |
| 2008/0208138 A1 | 8/2008 | Lim et al. | |

OTHER PUBLICATIONS

International Search Report and Written Opinion for PCT/US2011/022588 the counterpart application mailed on Oct. 18, 2011.

* cited by examiner

*Primary Examiner* — Christopher D Koharski

(57) ABSTRACT

A needle guide system comprising a needle guide including at least one wall defining an internal cavity and an outside of the needle guide. A lock is connected to the needle guide. The lock is movable between a first and a second position. A needle is disposed in the internal cavity of the needle guide, the needle having a long axis and a tip. The needle is movable along the long axis with respect to the needle guide when the lock is in the first position and the needle is locked to the needle guide and the tip extends beyond the wall of the needle guide when the lock is in the second position. Visual indicia on the lock may indicate whether the lock is in the first or the second position.

18 Claims, 2 Drawing Sheets

NEEDLE GUIDE SYSTEM

TECHNICAL FIELD

The present disclosure generally relates to a guide for needle insertion, and more particularly to a needle guide system effective to retain an inserted needle at a proper depth inside a patient.

BACKGROUND

Needles may be used to transfer an agent, drug or other substance into a patient. The needle may be inserted into the patient at a desired location. The needle may be hollow and include a hollow tip. A syringe with a drug may be attached to an end of the needle so that the drug may flow from the syringe, through the hollow needle, through the needle tip and into the patient.

An epidural injection, or epidural steroid injection, may be used to help reduce the pain caused by a herniated disc, degenerative disc disease, or spinal stenosis. These spinal disorders often affect the cervical (neck) and lumbar (lower back) areas of the spine.

The medicine used in the injection is usually a combination of a local anesthetic (e.g. bupivacaine) and a steroid (e.g. triamcinolone). The technique and risks of the procedure are similar to those for standard epidural analgesia. The technique is believed to work by reducing the inflammation or swelling, or both, of the nerves in the epidural space.

Needle placement for epidurals around the spine and nerve roots are typically performed under fluoroscopic guidance. A needle may be inserted near the spine and a practitioner may consult a fluoroscope display to ensure that the needle placement is at the proper location and depth. The fluoroscope provides a display so as to avoid inadvertently inserting the needle within adjacent nerve structures.

An example application of needle placement is the injection of epidural steroid drugs near compressed and inflamed nerve roots to treat sciatica, back pain or leg pain. In such a procedure, the doctor first inserts a needle into a patient at a desired location. A syringe with a drug may be connected to the needle. Thereafter, the doctor may exchange the syringe with another syringe to inject different compounds into the patient during the procedure. The present disclosure describes an improvement over these prior art technologies.

SUMMARY OF THE INVENTION

Accordingly, a guide for needle insertion is provided, and more particularly to a needle guide system effective to retain an inserted needle at a proper depth inside a patient.

One embodiment of the disclosure a needle guide system comprising a needle guide including at least one wall defining an internal cavity of the needle guide; a lock connected to the needle guide, the lock movable between a first and a second position; and a needle disposed in the internal cavity of the needle guide, the needle having a long axis and a tip. The needle is movable along the long axis with respect to the needle guide when the lock is in the first position. The needle is locked to the needle guide and the tip extends beyond the wall of the needle guide when the lock is in the second position.

Another embodiment of the disclosure is a method for inserting a needle into a patient. The method comprises inserting a needle into an internal cavity of a needle guide, the needle guide including at least one wall defining the internal cavity, the needle having a long axis and a tip, the inserting the needle including moving the needle along the long axis. The method further comprises inserting the needle into a patient; moving a lock connected to the needle guide from a first position to a second position to lock the needle to the guide when the tip extends beyond the wall of the needle guide; and connecting a syringe to the needle.

Yet another embodiment of the disclosure is a needle guide comprising at least one wall defining an internal cavity of the needle guide; and a lock, the lock movable between a first and a second position. The needle guide is effective to receive a needle in the internal cavity, the needle having a long axis and a tip. The lock is effective to allow the needle to move along the long axis with respect to the needle guide when the lock is in the first position. The lock is effective to lock the needle to the needle guide where the tip extends beyond the wall of the needle guide when the lock is in the second position. The lock including visual indicia indicating whether the lock is in the first or the second position.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

Figure 1:
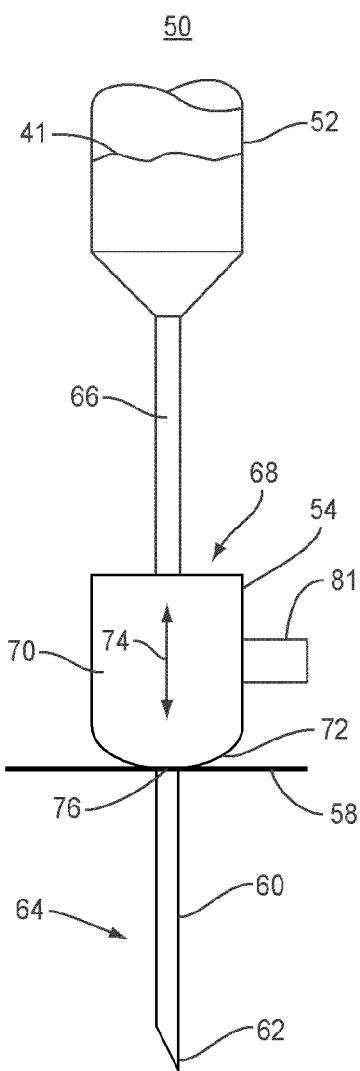
FIG. 1 is a side view of one particular embodiment of a needle, guide and syringe in accordance with the principles of the present disclosure.

The exemplary embodiments of the needle guide system and methods of use disclosed are discussed in terms of medical treatment devices and more particularly, in terms of a needle guide system and method for treating the spine.

It is envisioned that the guide system and methods of use disclosed provide improved guidance for a needle inserted in a patient. It is further envisioned that the present disclosure may be employed to treat musculoskeletal disorders including sacro-Iliac dysfunction or syndrome, dehydration, destabilization, laxity, fracture, tumor, spinal disorders and other orthopedic disorders. It is contemplated that the present disclosure may be employed with surgical treatments, including open surgery, percutaneous procedures involving use of a needle or cannula, percutaneous and minimally invasive procedures of such disorders, such as, for example, arthroplasty to maintain motion, arthrodesis including fusion, bone graft and implantable prosthetics. It is further contemplated that the present disclosure may be employed with other osteal and bone related applications, including those associated with diagnostics and therapeutics. The disclosed needle guide system and methods may be employed in a surgical treatment with a patient in a prone or supine position, employing a posterior, lateral, inferior, posterior-inferior, superior or anterior approach. The present disclosure may be employed with procedures for treating the lumbar, cervical, thoracic and pelvic regions of a spinal column.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

The following discussion includes a description of a needle guide system, related components and exemplary methods of employing the needle guide system in accordance with the principles of the present disclosure. Alternate embodiments are also disclosed. Reference will now be made in detail to the exemplary embodiments of the present disclosure, which are illustrated in the accompanying figures. Turning now to FIGS. 1-6B, there are illustrated components of the needle guide system in accordance with the principles of the present disclosure.

The components of the needle guide system are fabricated from materials suitable for medical applications, including metals, synthetic polymers, ceramics, bone, biocompatible materials and/or their composites, depending on the particular application and/or preference of a medical practitioner. The components of the needle guide system, such as the guide, lock and/or needle, discussed below, may be monolithically formed, integrally connected or configured as an insert. Different components of the needle guide system may have alternative material composites to achieve various desired characteristics such as strength, rigidity, elasticity, compliance, biomechanical performance, durability and radiolucency or imaging preference. The components of the needle guide system may also be fabricated from a heterogeneous material such as a combination of two or more of the above-described materials.

It has been discovered that in prior art systems as a practitioner disconnects and connects syringes, the force applied to an inserted needle can lead to the needle migrating further into the patient. Such migration may occur without the practitioner's knowledge, possibly leading to complications if the needle tip enters a nerve or vascular structure.

Referring to FIG. 1, a needle guide system 50 in accordance with the disclosure includes a needle 64, a syringe 52 and a guide 54. Needle 64 includes a needle end 66, a needle body 60 and a needle tip 62. Needle 64 has a long axis 74.

Guide 54 includes an opening 68, a body 70 and a tip 72. Syringe 52 may be detachably connected to needle 64 such as by friction fit, screw and thread, tongue and groove, protuberance and/or hole arrangements. Syringe 52 is shown as having a shape that is a combination of a cut-off hollow cylinder and a funnel. Other shapes and arrangements could also be used for syringe 52 such as, for example, ellipsoids, rectangular solids, pyramids, cylinders, frustums, or any other shape.

In the embodiment shown, body 70 of guide 54 includes at least one wall, such as, for example, a wall 55 defining a substantially hollow cylinder with an internal cavity 57. Tip 72 is shown as being hemispherical shape including an arcuate portion 76. Arcuate portion 76 allows needle 64 and guide 54 to be placed oblique to skin surface 58.

Arcuate portion 76 is curved or rounded to allow needle 64 to be angled at a desired position to locate tip 62 to penetrate the intended target, for example, under fluoroscopic guidance. However, other shapes and arrangements for body 70 and tip 72 could also be used. For example, ellipsoids, rectangular solids, pyramids, cylinders, frustums, or any shape could be used for either or both body 70 and tip 72. It is contemplated that the surface of tip 72 can be smooth and continuous, planar, textured, dimpled, rough, staggered, offset and/or coated with therapeutic agents and/or pharmacological agents.

Figure 2:
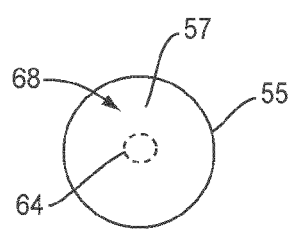
FIG. 2 is a top cut-away view of the guide shown in FIG. 1.

Referring also to FIG. 2, opening 68 and body 70 of guide 54 may be larger than a diameter of needle 64 so that needle 64 can move longitudinally along axis 74 relative to guide 54. It is contemplated that opening 68 may be variously sized and configured according to a particular needle application. It is further contemplated that tip 72 and/or portions thereof adjacent opening 68 may be rigid, semi-rigid and/or flexible to facilitate targeting and guidance of needle 64 to a random or pre-selected location.

Needle guide 54 is employed to prevent movement of needle 64 relative to needle guide 54 and relative to a patient. Undesired movement of needle 64 in the patient can lead to needle migration and inadvertent penetration, which can lead to patient complications and associated health risks. The needle guide system includes a lock 56 that is connected to needle guide 54. Lock 56 may be disposed on any portion of guide 54.

Lock 56 defines an elongated shaft 75, which is configured for lateral, slidable movement through side openings 77 of wall 55. Openings 77 are configured for slidable movement of shaft 75 therein. It is contemplated that the cross-sectional geometry of shaft 75 may have various configurations, for example, round, oval, oblong, triangular, rectangular, polygonal, irregular, uniform, non-uniform, consistent or variable. It is further contemplated that the diameter or thickness of shaft 75 may be offset, tapered, converging and/or diverging. Lock 56 may have a linear locking pin configuration and/or include angled portions for locking engagement with wall 55.

Shaft 75 has a circumferential outer surface 81, which includes a continuous first diameter portion 84. Portion 84 extends continuously, having a smooth, even configuration, to an arcuate portion 82, which has a reduced diameter relative to first diameter portion 84. Arcuate portion 82 gradually decreases in diameter and tapers to a minimum dimension, and continues to extend to gradually increase in diameter to an opposing portion of first diameter portion 84. The surface of arcuate portion 82 is configured to receive needle 64 for slidable relative engagement. The surface of portion 84 is configured to engage needle 64 in a friction or interference engagement to fix the position of needle 64 relative to needle guide 54.

Arcuate portion 82 defines a diameter that is smaller than the diameter defined by portion 84. It is contemplated that outer surface 81, the surface of portion 84 and/or the surface of portion 82 may individually or collectively be smooth, textured, planar and/or rough.

Figure 3:
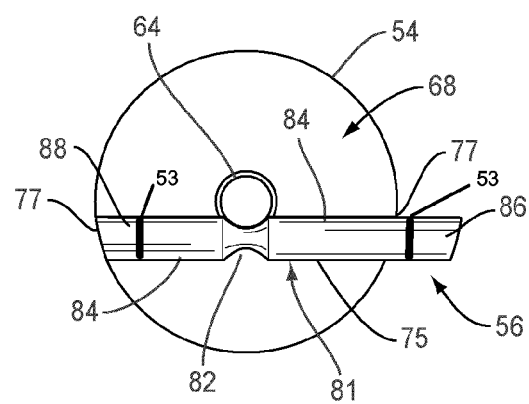
FIG. 3 is a top cut-away view of the guide shown in FIG. 1.
Figure 4:
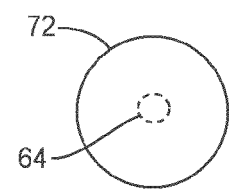
FIG. 4 is a top cut-away view of the guide shown in FIG. 1.

Needle 64 is inserted into needle guide 54 and can move relative to guide 54 along axis 74 (FIG. 1) when lock 56 is in a first position so that needle 64 is disposed in arcuate portion 82. Arcuate portion 82 allows movement of needle 64. Needle 64 tends to remain toward a center of guide 54 because tip 72 includes walls maintaining needle 64 in a center of guide 54 as shown in FIG. 4. When lock 56 is moved to a second position so that needle 64 engages the outer surface of portion 84, friction between the surfaces of portion 84 and needle 64 inhibit movement of needle 64 along axis 74. A user may thus lock needle 64 with respect to needle guide 54 by engaging lock 56 into the second, locked position. For example, as shown in FIG. 3, lock 56 may be moved from right to left to engage portion 84 with needle 64.

Lock 56 includes visual indicia 53 to indicate that needle 64 is a first position, free to slidably move relative to guide 54 and/or needle 64 is a second position such that needle 64 is locked and fixed relative to guide 54. Lock 56 is color coded to provide such visual indicia 53.

A first side 86 of lock 56 includes a first color, such as, for example, the color green. A second side 88 of lock 56 includes a second color, such as, for example the color red. In this way, when the portion of first side 86 including green color extends outside of opening 77 and beyond wall 55 of guide 54, visual indicia 53 including the color green will be provided to the practitioner. The green color indicates that needle 64 is movable relative to guide 54 because needle 64 is disposed in engagement with arcuate portion 82.

When the portion of second side 88 including red color extends outside opening 77 and beyond wall 55 of guide 54, visual indicia 53 including the color red will be provided to the practitioner. The red color indicates that needle 64 is locked and because needle 64 disposed in a frictional or interference engagement with portion 84 and is fixed relative to guide 54. It is envisioned that various colors may be employed. It is further envisioned that alternate visual indicia 53 may be used such as shapes and/or graduated markings. It is contemplated that tactile or audible indicia may also be employed.

Figure 5A:
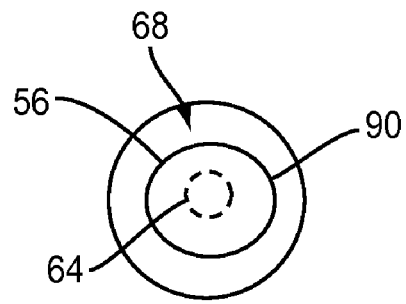
FIGS. 5A and 5B are top cut-away views of the guide shown in FIG. 1.
Figure 5B:
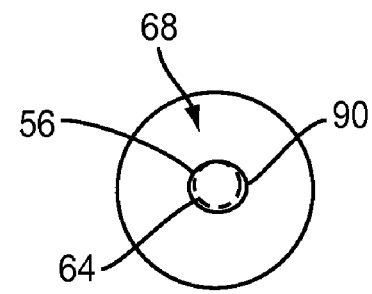
Figure 6A:
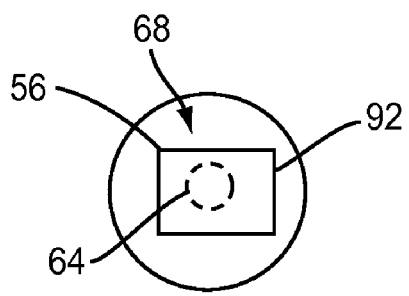
FIGS. 6A and 6B are top cut-away views of the guide shown in FIG. 1.
Figure 6B:
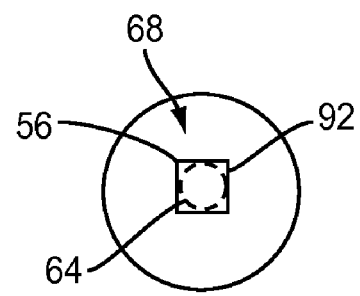

Other structures may be used for lock 56. For example, arcuate portion 82 may be removed from lock 56. In this way, needle 64 is free to move relative to guide 54 except when portion 84 is engaged with needle 64. In other examples, as shown in FIGS. 5A, 5B, 6A and 6B, lock 56 may include an adjustable internal void. Walls 90, 92 defining the void may be moved to engage or release needle 64. For example, the void may be defined by a hollow cylinder, straight walls and/or curved walls. FIGS. 5A and 5B show examples where lock 56 includes an adjustable void defined by curved walls 90. FIGS. 6A and 6B show examples where lock 56 includes an adjustable void defined by straight walls 92. In one embodiment, needle guide system 50, similar to that described above, includes a rotation mechanism, such as, for example, a knurled wheel connected or attached to guide 54. The knurled wheel is rotated, via manipulation or mechanical control, to cause an internal mechanism, such as, for example, a lever or shaft, such as, lock 56 described herein, to lock needle 64 in a desired position/orientation. In one embodiment, needle guide system 50, similar to that described above includes a lever extending from guide 54. The lever is movable to cause an internal mechanism, described above, to lock needle in a desired position/orientation.

Referring again to FIG. 1, in use during administration of an epidural application, needle 64 may be placed at an inside of body 70 of guide 54 prior to insertion of needle 64 attached to a catheter into a patient. A practitioner identifies a suitable anatomical gap between the bony spinous processes prior to the procedure. A target location for needle penetration is determined. The level of the spine at which needle 64 is placed depends on the needle site and type of an intended operation or the anatomical origin of pain.

The practitioner conducting an epidural places the catheter in the mid-lumbar, or lower back region of the spine. The patient's skin may be infiltrated with local anaesthetic such as lidocaine over the identified space. The insertion point is usually in the midline, although other approaches, such as the paramedian approach, may occasionally be employed.

As distal tip 72 includes curved portion 76, such that the combination of guide 54 and needle 64 may be angled at a desired position relative to an intended target. For example, the combination may be moved with respect to skin surface 58 so that axis 74 of needle 64 may be inserted oblique to skin surface 58. Lock 56 is in the first position such that the portion of first side 86 including green color extends outside of opening 77 and beyond wall 55 of guide 54, thereby providing visual indicia 53 including the color green to the practitioner.

The green color indicates that needle 64 is movable relative to guide 54 because needle 64 is disposed in engagement with arcuate portion 82. Needle 64 is inserted through skin surface 58 under fluoroscopic guidance. When needle 64 is at its desired location, lock 56 may be engaged to lock needle 64 in a fixed position relative to guide 54 to prevent undesired movement of needle 64 relative to needle guide 54 and relative to a patient, such as needle migration and inadvertent penetration, which can lead to patient complications and associated health risks.

Lock 56 is pushed or engaged so that portion 84 frictionally engages needle 64. The portion of second side 88 including red color extends outside opening 77 and beyond wall 55 of guide 54, thereby providing visual indicia 53 including the color red to the practitioner. The red color indicates that needle 64 is locked because needle 64 disposed in a frictional or interference engagement with portion 84 and is fixed relative to guide 54.

This movement also moves first side 86, with green color, inside of guide 54 and moves second side 88, with a red color, outside of guide 54. Such locking prevents needle 64 from inadvertently being pushed deeper into a patient. Needle tip 62 extends beyond wall 55. Syringe 52 including a pharmacological and/or therapeutic agent 41 may be selectively connected to and/or disconnected from needle 64.

If a practitioner desires to reposition needle 64, lock 56 may be disengaged. Lock 56 is engaged at the portion of second side 88 including red color so that second side 88 is pushed inside of guide 54 and first side 86 extends outside of guide 54. Needle 64 is freely slidable relative to guide 54. An alternate syringe may be connected to needle 64, and/or needle 64 and guide 54 can be removed from a patient. Needle 64 may thereafter be removed from guide 54 by disengaging lock 56. In one embodiment, guide 54 is fabricated, includes an outer layer and/or is coated with a radiolucent material such as a polymer, in a configuration such that guide 54 is not detected during fluoroscopic imaging. In one embodiment, the components of needle guide system 50 such as, for example, guide 54 includes one or a plurality of sensors mounted therewith that are detectable so that guide 54 can be detected and/or the trajectory of needle 64 can be tracked using three-dimensional stereotactic equipment for accurate placement of needle tip 62. The sensors may include LCD sensors and/or other detectable biocompatible sensors.

It is envisioned that the components of the needle guide system can be manufactured via various methods. For example, the components of the needle guide system can be manufactured and assembled via injection-molding, insert-molding, overmolding, compression molding, transfer molding, co-extrusion, pultrusion, dip-coating, spray-coating, powder-coating, porous-coating, milling from a solid stock material, and their combinations. One skilled in the art, however, will realize that such materials and fabrication methods suitable for assembly and manufacture, in accordance with the present disclosure, would be appropriate.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A needle guide system comprising:
   a needle guide including at least one wall defining an internal cavity of the needle guide;
   a lock connected to the needle guide, the lock movable between a first and a second position and having a shaft including a first end and a second end; and
   a needle disposed in the internal cavity of the needle guide, the needle having a long axis and a tip; wherein
   the needle is movable along the long axis with respect to the needle guide when the lock is in the first position; and
   the needle is locked to the needle guide and the tip extends beyond the wall of the needle guide when the lock is in the second position, wherein when the lock is in the first position, the first end is disposed in the internal cavity of the needle guide and the second end is disposed external to the internal cavity of the needle guide, and when the lock is in the second position, the second end is disposed in the internal cavity of the needle guide and the first end is disposed external to the internal cavity of the needle guide.

2. The system as recited in claim 1, wherein the lock includes a shaft, the shaft including an arcuate portion and a continuous portion having a larger diameter than the diameter of the arcuate portion.

3. The system as recited in claim 2, wherein in the first position, the arcuate portion engages the needle.

4. The system as recited in claim 3, in the second position, the continuous portion frictionally engages the needle.

5. The system as recited in claim 4, wherein in the first position, the shaft includes a first visual indicia and in the second position, the shaft includes a second visual indicia.

6. The system as recited in claim 5, wherein the shaft includes a first end with the first visual indicia and a second end with the second visual indicia.

7. The system as recited in claim 1, in the second position, the lock including a surface configured to frictionally engage the needle.

8. The system as recited in claim 1, wherein the guide includes a tip with an arcuate surface configured to engage a body surface.

9. The system as recited in claim 1, wherein the lock includes an outer surface defining a void configured to receive the needle in the first position, the outer surface being adjustable to move the lock between the first and second positions such that the needle enters and exits the void.

10. The system as recited in claim 1, wherein at least a portion of the needle guide is radiolucent.

11. The system as recited in claim 1, wherein the needle guide includes at least one detectable sensor.

12. A method for inserting a needle into a patient, the method comprising:
    inserting a needle into an internal cavity of a needle guide, the needle guide including at least one wall defining the internal cavity, the needle having a long axis and a tip, the step of inserting the needle further including moving the needle along the long axis;
    inserting the needle into a patient;
    engaging a lock connected to the needle guide to move the lock from a first position to a second position to lock the needle to the guide when the tip extends beyond the wall of the needle guide, the lock having a first end and a second end; and connecting a syringe to the needle, wherein when the lock is in the first position, the first end is disposed within the interior cavity of the needle guide and the second end is disposed external to the needle guide, and when the lock is in the second position, the second end is disposed within the interior cavity and the first end is disposed external to the needle guide.

13. The method as recited in claim 12, further comprising:
    moving the lock from the second position to the first position;
    moving the needle with respect to the guide along the long axis; and
    moving the lock from the second position to the first position.

14. The method as recited in claim 12, wherein the lock includes a shaft, the shaft including an arcuate portion and a continuous portion having a larger relative diameter.

15. The method as recited in claim 14, wherein in the first position, the shaft includes a first visual indicia and in the second position, the shaft includes a second visual indicia.

16. The method as recited in claim 12, wherein:
    the guide includes a tip having an arcuate surface; and
    further comprising the step of adjusting the guide relative to the patient prior to inserting the needle so that the long axis of the needle is oblique to a surface of the patient.

17. The method as recited in claim 12, wherein the lock includes a wall defining a void configured to receive the needle in the first position, the wall being adjustable to move the lock between the first and second positions such that the needle enters and exits the void.

18. A needle guide comprising:
    at least one wall defining an internal cavity of the needle guide; and
    a lock, the lock movable between a first and a second position and having a first end and a second end; wherein
    the needle guide is effective to receive a needle in the internal cavity, the needle having a long axis and a tip;
    the lock is effective to allow the needle to move along the long axis with respect to the needle guide when the lock is in the first position;
    the lock is effective to lock the needle to the needle guide where the tip extends beyond the wall of the needle guide when the lock is in the second position; and
    the lock including visual indicia indicating whether the lock is in the first or the second position, wherein when the lock is in the first position, the first end is disposed in the internal cavity of the needle guide and the second end is disposed external to the internal cavity of the needle guide, and when the lock is in the second position, the second end is disposed in the internal cavity of the needle guide and the first end is disposed external to the internal cavity of the needle guide.

* * * * *

UNITED STATES PATENT AND TRADEMARK OFFICE
CERTIFICATE OF CORRECTION

| | | |
|---|---|---|
| PATENT NO. | : 8,267,895 B2 | Page 1 of 1 |
| APPLICATION NO. | : 12/693853 | |
| DATED | : September 18, 2012 | |
| INVENTOR(S) | : McKay | |

It is certified that error appears in the above-identified patent and that said Letters Patent is hereby corrected as shown below:

In Column 7, Line 41, in Claim 4, delete "in the" and insert -- wherein in the --, therefor.

Signed and Sealed this
Twenty-third Day of October, 2012

David J. Kappos
*Director of the United States Patent and Trademark Office*